(12) United States Patent
Lakshmi

(10) Patent No.: US 7,658,994 B2
(45) Date of Patent: Feb. 9, 2010

(54) SUBSTRATES AND COMPOUNDS BONDED THERETO

(75) Inventor: Brinda B. Lakshmi, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 361 days.

(21) Appl. No.: 10/896,392

(22) Filed: Jul. 22, 2004

(65) Prior Publication Data

US 2005/0142296 A1    Jun. 30, 2005

Related U.S. Application Data

(60) Provisional application No. 60/533,178, filed on Dec. 30, 2003.

(51) Int. Cl.
B32B 7/12      (2006.01)
B32B 15/04     (2006.01)
B32B 3/26      (2006.01)

(52) U.S. Cl. .................... 428/343; 428/304.4; 428/344; 428/355 R

(58) Field of Classification Search ................ 428/343, 428/344, 355 R, 304.4
See application file for complete search history.

(56) References Cited

U.S. PATENT DOCUMENTS

| | | | |
|---|---|---|---|
| 2,109,491 A * | 3/1938 | Lipkin ......................... 508/425 |
| 3,607,261 A * | 9/1971 | Amidon et al. ............... 430/76 |
| 3,619,371 A | 11/1971 | Crook et al. |
| 4,192,830 A | 3/1980 | Wolf |
| 4,204,041 A | 5/1980 | Bailey et al. |
| 4,211,677 A | 7/1980 | Rose et al. |
| 4,229,537 A | 10/1980 | Hodgins et al. |
| 4,539,256 A | 9/1985 | Shipman |
| 4,601,843 A | 7/1986 | Carr et al. |
| 4,708,858 A | 11/1987 | Kirkpatrick |
| 4,724,264 A | 2/1988 | Nakacho et al. |
| 4,986,914 A | 1/1991 | Franks |
| 5,120,594 A | 6/1992 | Mrozinski |
| 5,182,273 A | 1/1993 | Duflos et al. |
| 5,238,623 A | 8/1993 | Mrozinski |
| H1309 H | 5/1994 | Allen et al. |
| 5,531,878 A | 7/1996 | Vadgama et al. |
| 5,552,272 A | 9/1996 | Bogart |
| 5,639,671 A | 6/1997 | Bogart et al. |
| 5,965,683 A | 10/1999 | Nye et al. |
| 6,015,597 A | 1/2000 | David |
| 6,696,304 B1 | 2/2004 | Davies |
| 6,994,966 B2 | 2/2006 | Dukler et al. |
| 7,259,258 B2 | 8/2007 | Kozlov et al. |
| 2002/0055184 A1 | 5/2002 | Naylor et al. |
| 2003/0054181 A1 | 3/2003 | Swerdlow et al. |
| 2003/0218130 A1 | 11/2003 | Boschetti et al. |

FOREIGN PATENT DOCUMENTS

| | | |
|---|---|---|
| FR | 2705347 A1 | 11/1994 |
| JP | 5043600 | 2/1993 |
| WO | WO 95/19184 | 7/1995 |
| WO | WO 95/32736 | 12/1995 |
| WO | WO 98/14610 | 4/1998 |
| WO | WO 01/66244 | 9/2001 |
| WO | WO01/66820 | 9/2001 |
| WO | WO03/050237 | 6/2003 |
| WO | WO 03/091304 | 11/2003 |
| WO | WO 03/093785 | 11/2003 |

OTHER PUBLICATIONS

V. Chandrasekhar et al., Pyrazolylcyclotriphosphazene Containing Pendant Polymers: Synthesis, Characterization, and Phosphate Ester Hydrolysis Using a Cu(II)-Metalated Cross-Linked Polymeric Catalyst, Inorganic Chemistry Article, vol. 41, No. 20, 2002, pp. 5162-5173.

K.C. Das; Y. Lin; B. Weinstein, Experientia, "A New Peptide Coupling Agent—Phosphonitrilic Chloride," Dec. 15, 1969, pp. 1238-1239.

H.-D. Hunger, CH. Coutelle, G. Behrendt, CHR. Flachmeier, A. Rosenthal, A. Speer, H. Breter, R. Szargan, P. Franke, J. Stahl, N.V. Cuong, and G. Barchend, Analytical Biochemistry, "CCA Paper: A New Two-Dimensional Cyanuric Chloride-Activated Matrix for Universal Application in Molecular Biology," Nov. 13, 1985, pp. 286-299.

(Continued)

Primary Examiner—Victor S Chang

(57) ABSTRACT

Articles and methods for the use of such articles are described for use in immobilizing nucleophile-containing materials. In one aspect, the invention provides an article comprising: a substrate having a first surface and a second surface; and a phosphonitrilic tethering group affixed to the first surface of the substrate, the phosphonitrilic tethering group comprising a reaction product of a complementary functional group on the first surface of the substrate with a phosphonitrilic tethering compound. A method of immobilizing a nucleophile-containing material to a substrate is also described, the method comprising: providing a phosphonitrilic tethering compound; providing a substrate having a complementary functional group capable of reacting with phosphonitrilic tethering compound; preparing a substrate-attached phosphonitrilic tethering group by reacting the phosphonitrilic tethering compound with the complementary functional group on the substrate resulting in an ionic bond, covalent bond, or combinations thereof; and reacting the substrate-attached phosphonitrilic tethering group with a nucleophile-containing material to immobilize the nucleophile-containing material.

7 Claims, No Drawings

OTHER PUBLICATIONS

H. Allcock and S. Kwon, Macromolecules 1986, "Covalent Linkage of Proteins to Surface-Modified Poly(organophosphazenes): Immobilization of Glucose-6-Phosphate Dehydrogenase and Trypsin," Jan. 7, 1986, pp. 1502-1508.

H.-D. Hunger, A. Speer, CHR. Flachmeier, R. Hanke, G. Behrendt, and CH. Coutelle, Analytical Biochemistry, "Use of Cyanuric Chloride-Activated Paper for Detection of Subpicogram Quantities of Specific DNA Sequences and Its Application to Linked Restriction Fragment Length Polymorphism Analysis in a Duchenne Muscular Dystrophy Affected Family," Oct. 6, 1986, pp. 45-55.

J. Van Ness, S. Kalbfleisch, C. Petrie, M. Reed, J. Tabone and N. Vermeulen, Nucleic Acids Research, vol. 19, No. 12, "A Versatile Solid Support System for Oligodeoxynucleotide Probe-Based Hybridization Assays," Mar. 5, 1991, pp. 3345-3350.

J. Mark, H. Allcock, R. West, Inorganic Polymers, Polymeric Science & English Series, Chapter 3, "Polyphosphazenes," 1992, pp. 60-140.

H. Allcock, C. Nelson, & W. Coggio, Chemistry of Materials, 1994, 6. "Photoinitiated Graft Poly(organophosphazenes): Functionalized Immobilization Substrates for the Binding of Amines, Proteins, and Metals," Jul. 15, 1993, pp. 516-524.

H. Baek, Y. Cho, C. Lee, & Y. Sohn, Anti-Cancer Drugs 2000, vol. 11, "Synthesis and Antitumor Activity of Cyclotriphosphazene-(diamine)platinum(II) Conjugates," pp. 715-725.

Scham D. et al., "Spatially Addressed Synthesis of Amino- and Amino-Oxy-Substituted 1,3,5-Triazine Arrays on Polymeric Membranes", *Journal of Combinatorial Chemistry American Chemical Society*, vol. 2, Jun. 2000, pp. 361-369.

Stankova M. et al., "Library Generation Through Successive Substitution of Trichlorotriazine", *Molecular Diversity*, vol. 2, No. 1/2, 1996, pp. 75-80.

\* cited by examiner

SUBSTRATES AND COMPOUNDS BONDED THERETO

This application claims the benefit of U.S. Provisional Application No. 60/533,178, filed Dec. 30, 2003.

FIELD OF THE INVENTION

The invention relates to articles comprising a substrate having a tethering group affixed to the substrate and to methods for immobilizing a nucleophile-containing material to the substrate.

BACKGROUND OF THE INVENTION

The covalent attachment of biologically active molecules to the surface of a substrate can be useful in a variety of applications such as in diagnostic devices, affinity separations, high throughput DNA sequencing applications, the clean-up of polymerase chain reactions (PCR), and the like. Immobilized biological amines, for example, can be used for the medical diagnosis of a disease or genetic defect or for detection of various biomolecules.

The modification of solid supports (e.g. particulate chromatography supports) by introduction of reactive functional groups for the immobilization of any of a variety of ligands is known. The attachment of a nucleophile (e.g., NH2, SH, OH, etc.) to a substrate may be achieved through the use of tethering compounds. A tethering compound has at least two reactive functional groups separated by a linking group. One of the functional groups provides a means for anchoring the tethering compound to a substrate or support by reacting with a complementary functional group on the surface of the substrate. A second reactive functional group can be selected to react with the nucleophile-containing material. Supports containing hydroxyl groups (e.g. cellulose, cross-linked dextrans, wool, and polyvinyl alcohol) may be treated with cyanuric chloride (trichlorotriazine) for the attachment of enzymes, antigens, and antibodies. Hydroxyl-containing supports such as Sepharose may be reacted with trichlorotriazine (TCT) which may then bind one or more nucleophiles. Solid nylon beads derivatized with cyanuric chloride have been used for oligonucleotide based hybridization assays. TCT coated paper and nylon membranes have also demonstrated utility in transfer hybridization experiments of DNA, RNA, and proteins.

Known tethering compounds are typically highly reactive with nucleophile-containing materials including biological materials. But, the reaction of the tethering compounds to nucleophile-containing materials may compete with other reactions, such as the hydrolysis of the tethering compound, when reactions with nucleophiles are conducted in aqueous solutions. Hydrolysis can result in incomplete or inefficient immobilization of the nucleophile-containing materials on a substrate.

There is a need for improved immobilization substrates and for tethering compounds compatible with such substrates. Accordingly, it is desired to provide supports and tethering compounds that are useful for ligand immobilization in any of a variety of applications.

SUMMARY OF THE DISCLOSURE

The present invention provides articles and methods for the use of such articles in immobilizing nucleophile-containing materials such as amine-containing analyte, amino acid, peptide, DNA, RNA, protein, enzyme, organelle, immunoglobulin, and fragments and combinations of two or more of the foregoing. The nucleophile-containing material may comprise an amine-containing material such as, for example, an antigen (including an antigen bound to an antibody), an immunoglobulin or the like. In some embodiments, the amine-containing material may be further bound to a bacterium such as *Staphylococcus aureus*.

In one aspect, the invention provides an article comprising:
a substrate having a first surface and a second surface;
a phosphonitrilic tethering group attached to the first surface of the substrate, the phosphonitrilic tethering group comprising a reaction product of a functional group on the first surface of the substrate with a phosphonitrilic tethering compound.

In some embodiments, the phosphonitrilic tethering compound comprises a structure according to Formula I

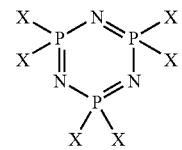

Wherein each X may be the same or different and comprise reactive groups susceptible to nucleophilic attack to bond with a nucleophile-containing material.

In another aspect, the invention provides a method of immobilizing a nucleophile-containing material to a substrate, the method comprising:
Providing a phosphonitrilic tethering compound;
Providing a substrate having a functional group capable of reacting with the phosphonitrilic tethering compound;
Preparing a substrate-attached phosphonitrilic tethering group by reacting the phosphonitrilic tethering compound with the functional group on the substrate resulting in an ionic bond, covalent bond, or combinations thereof; and
Reacting the substrate-attached phosphonitrilic tethering group with a nucleophile-containing material to immobilize the nucleophile-containing material.

Certain terms used in the description of the invention will be understood as having the following meanings:

As used herein, the terms "a", "an", and "the" are used interchangeably with "at least one" to mean one or more of the elements being described.

As used herein, the term "acyl" refers to a monovalent group of formula —(CO)R where R is an alkyl group and where (CO) used herein indicates that the carbon is attached to the oxygen with a double bond.

As used herein, the term "acyloxy" refers to a monovalent group of formula —O(CO)R where R is an alkyl group.

As used herein, the term "acyloxysilyl" refers to a monovalent group having an acyloxy group attached to a Si (i.e., Si—O(CO)R where R is an alkyl). For example, an acyloxysilyl can have a formula —Si[O(CO)R]$_{3-n}$L$_n$ where n is an integer of 0 to 2 and L is a halogen or alkoxy. Specific examples include —Si[O(CO)CH$_3$]$_3$, —Si[O(CO)CH$_3$]$_2$Cl, or —Si[O(CO)CH$_3$]Cl$_2$.

As used herein, the term "alkoxy" refers to a monovalent group of formula —OR where R is an alkyl group.

As used herein, the term "alkoxycarbonyl" refers to a monovalent group of formula —(CO)OR where R is an alkyl group.

As used herein, the term "alkoxysilyl" refers to a group having an alkoxy group attached to a Si (i.e., Si—OR where R is an alkyl). For example, an alkoxysilyl can have a formula —Si(OR)$_{3-n}$(L$^a$)$_n$ where n is an integer of 0 to 2 and L$^a$ is a halogen or acyloxy. Specific examples include —Si(OCH$_3$)$_3$, —Si(OCH$_3$)$_2$Cl, or —Si(OCH$_3$)Cl$_2$.

As used herein, the term "alkyl" refers to a monovalent radical of an alkane and includes groups that are linear, branched, cyclic, or combinations thereof. The alkyl group typically has 1 to 30 carbon atoms. In some embodiments, the alkyl group contains 1 to 20 carbon atoms, 1 to 10 carbon atoms, 1 to 6 carbon atoms, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

As used herein, the term "alkyl disulfide" refers to a monovalent group of formula —SSR where R is an alkyl group.

As used herein, the term "alkylene" refers to a divalent radical of an alkane. The alkylene can be straight-chained, branched, cyclic, or combinations thereof. The alkylene typically has 1 to 200 carbon atoms. In some embodiments, the alkylene contains 1 to 100, 1 to 80, 1 to 50, 1 to 30, 1 to 20, 1 to 10, or 1 to 4 carbon atoms. The radical centers of the alkylene can be on the same carbon atom (i.e., an alkylidene) or on different carbon atoms.

As used herein, "aminosilane" refers to refers to a group having an amine group attached to a Si. For example, an aminosilane can have a formula —Si(OR$^1$)$_{3-n}$[(R$^2$)NH$_2$]$_n$ where n is an integer of 0 to 2 and R$^1$ is an alkyl having a carbon chain length less than 5, R$^2$ is another alkyl group having a carbon chain length of at least 2. Specific examples include 3-aminopropyl triethoxysilane, 3-amino trimethoxy silane.

As used herein, the term "aralkyl" refers to a monovalent radical of the compound R—Ar where Ar is an aromatic carbocyclic group and R is an alkyl group.

As used herein, the term "aralkylene" refers to a divalent radical of formula —R—Ar— where Ar is an arylene group and R is an alkylene group.

As used herein, the term "aryl" refers to a monovalent aromatic carbocyclic radical. The aryl can have one aromatic ring or can include up to 5 carbocyclic ring structures that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

As used herein, the term "arylene" refers to a divalent radical of a carbocyclic aromatic compound having one to 5 rings that are connected, fused, or combinations thereof. In some embodiments, the arylene group has up to 5 rings, up to 4 rings, up to 3 rings, up to 2 rings, or one aromatic ring. For example, the arylene group can be phenylene.

As used herein, the term "azido" refers to a group of formula —N$_3$.

As used herein, the term "aziridinyl" refers to a cyclic monovalent radical of aziridine having the formula

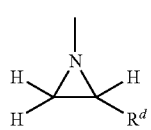

where R$^d$ is hydrogen or alkyl.

As used herein, the term "benzotriazolyl" refers to a monovalent group having a benzene group fused to a triazolyl group. The formula for a benzotriazolyl group is C$_6$H$_4$N$_3$—.

As used herein, the term "carbonyl" refers to a divalent group of formula —(CO)—.

As used herein, the term "carbonylimino" refers to a divalent group of the formula —(CO)NR$^4$— where R$^4$ is hydrogen, alkyl, or aryl.

As used herein, the term "carbonyloxy" refers to a divalent group of formula —(CO)O—.

As used herein, the term "carbonyloxycarbonyl" refers to a divalent group of formula —(CO)O(CO)—. Such a group is part of an anhydride compound.

As used herein, the term "carbonylthio" refers to a divalent group of formula —(CO)S—.

As used herein, the term "carboxy" refers to a monovalent group of formula —(CO)OH.

As used herein, the term "chloroalkyl" refers to an alkyl having at least one hydrogen atom replaced with a chlorine atom.

As used herein, the term "cyano" refers to a group of formula —CN.

As used herein, the term "disulfide" refers to a divalent group of formula —S—S—.

As used herein, the term "ethylenically unsaturated" refers to a monovalent group having a carbon-carbon double bond of formula —CY=CH$_2$ where Y is hydrogen, alkyl, or aryl.

As used herein, the term "fluoroalkyl" refers to an alkyl having at least one hydrogen atom replaced with a fluorine atom.

As used herein, the term "haloalkyl" refers to an alkyl having at least one hydrogen atom replaced with a halogen selected from F, Cl, Br, or I. Perfluoroalkyl groups are a subset of haloalkyl groups.

As used herein, the term "halocarbonyloxy" refers to a monovalent group of formula —O(CO)X where X is a halogen atom selected from F, Cl, Br, or I.

As used herein, the term "halocarbonyl" refers to a monovalent group of formula —(CO)X where X is a halogen atom selected from F, Cl, Br, or I.

As used herein, the term "halosilyl" refers to a group having a Si attached to a halogen (i.e., Si—X where X is a halogen). For example, the halosilyl group can be of formula —SiX$_{3-n}$(L$^b$)$_n$ where n is an integer of 0 to 2 and L$^b$ is selected from an alkoxy, or acyloxy. Some specific examples include the groups —SiCl$_3$, —SiCl$_2$OCH$_3$, and —SiCl(OCH$_3$)$_2$.

As used herein, the term "heteroalkylene" refers to a divalent alkylene having one or more carbon atoms replaced with a sulfur, oxygen, or NR$^d$ where R$^d$ is hydrogen or alkyl. The heteroalkylene can be linear, branched, cyclic, or combinations thereof and can include up to 400 carbon atoms and up to 30 heteroatoms. In some embodiments, the heteroalkylene includes up to 300 carbon atoms, up to 200 carbon atoms, up to 100 carbon atoms, up to 50 carbon atoms, up to 30 carbon atoms, up to 20 carbon atoms, or up to 10 carbon atoms.

As used herein, the term "hydroxy" refers to a group of formula —OH.

As used herein, the term "isocyanato" refers to a group of formula —NCO.

As used herein, the term "mercapto" refers to a group of formula —SH.

As used herein, "nucleophile" or "nucleophile-containing material" refers to moieties with reactive oxygen, sulfur and/or nitrogen containing groups such as substituted amino groups. Examples of nucleophile-containing materials include those with moieties such as amino, alkyl or aryl substituted amino, alkylamino, arylamino, oxyalkyl, oxyaryl, thioalkyl, and thioaryl groups, residues of dyestuffs containing amino groups such as nitro-dyestuffs, azo-dystuffs, including thiazole dystuffs, acridine-, oxyazine-, thiazine- and azine dyestuffs, indigoids, aminoanthraquinones, aromatic diamines, aminophenols, aminonaphthols and N and O-acidyl or alkyl, aralkyl or aryl derivatives of these, nitramines, thiophenols, or amino mercaptans. Exemplary nucleophile-containing material include the following moieties: OCH2 COOH; NHCH$_2$COOH; SCH$_2$COOH; NHC$_2$H$_4$SO$_3$H; OC$_4$H$_8$N(C$_2$H$_5$)$_3$; NHC$_6$H$_4$SO$_3$H; OC$_6$H$_4$COOH; SC$_6$H$_4$COOH; NHC$_2$H$_4$OH; OC$_2$H$_4$OH; and NHC$_3$H$_6$NH(C$_2$H$_4$OH)$_2$.

As used herein, the term "oxy" refers to a divalent group of formula —O—.

As used herein, the term "perfluoroalkyl" refers to an alkyl group in which all of the hydrogen atoms are replaced with fluorine atoms. Perfluoroalkyl groups are a subset of fluoroalkyl groups.

As used herein, the term "phosphato" refers to a monovalent group of formula —OPO$_3$H$_2$.

As used herein, "phosphonitrilic moiety" or "phosphonitrilic group" refers to structures of the following general formula:

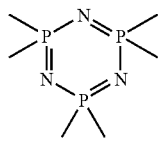

As used herein, "phosphonitrilic tethering compound" or "phosphonitrilic tethering group" refer to tethering compounds or tethering groups having at least one phosphonitrilic moiety or group.

As used herein, the term "phosphono" refers to a monovalent group of formula —PO$_3$H$_2$.

As used herein, the term "phosphoramido" refers to a monovalent group of formula —NHPO$_3$H$_2$.

As used herein, the term "primary aromatic amino" refers to a monovalent group of formula —ArNH$_2$ where Ar is an aryl group.

As used herein, the term "secondary aromatic amino" refers to a monovalent group of formula —ArNR$^h$H where Ar is an aryl group and R$^h$ is an alkyl or aryl.

As used herein, the term "tertiary amino" refers to a group of formula —NR$_2$ where R is an alkyl.

As used herein, the term "tethering compound" refers to a compound that has at least two reactive groups. One of the reactive groups (i.e., the substrate-reactive functional group) can react with a complementary functional group on the surface of a substrate to form a tethering group. Another reactive group can react either with a nucleophile-containing material, or another tethering compound (or a derivative or oligomer thereof) or another moiety capable of bonding with a nucleophile-containing material. Reaction of two reactive groups of the tethering compound results in the formation of a connector group between the substrate and a nucleophile-containing material such as an amine-containing material that is immobilized on the substrate.

As used herein, the term "tethering group" refers to a group attached to a substrate that results from the reaction of a tethering compound with a complementary functional group on the surface of the substrate with a tethering compound.

The foregoing summary is not intended to be inclusive of all possible embodiments of the invention. Those skilled in the art will more fully appreciate the features and advantages of the invention upon consideration of the remainder of the disclosure including the Detailed Description of the Preferred Embodiment, the various Examples and the appended claims.

DETAILED DESCRIPTION OF THE PREFERRED EMBODIMENT

The present invention provides articles and methods for immobilizing nucleophile-containing materials to a substrate. Phosphonitrilic compounds having reactive functional groups are described for use as tethering compounds between a substrate and at least one nucleophile-containing material. Tethering compounds useful in the invention comprise reactive groups susceptible to nucleophilic attack. At least one of the reactive functional groups on the tethering compound provides a means of attachment of the tethering compound to a surface of a substrate. The remaining functional groups can each be reacted with a nucleophile-containing material, such as amine functional proteins, enzymes, other biomolecules or the like. Additionally, the functional groups can be reacted with nucleophile-containing groups or can provide additional links to other moieties such as other similar tethering compounds or other reactive moieties which may be simple or complex in their structures (e.g., branched, straight chain, etc.) and typically including additional reactive groups that are also capable of bonding with nucleophile-containing materials.

In embodiments of the invention, tethering compounds for bonding biological molecules to the surface of a substrate comprise phosphonitrilic groups, and may be of the general composition of Formula I:

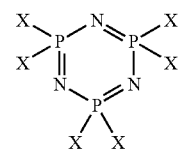

Wherein

Each X may be the same or different and comprise reactive groups susceptible to nucleophilic attack to bond with a nucleophile-containing material. Typically, X includes a halogen and most typically, X is chlorine.

Phosphonitrilic tethering compounds useful in the present invention include phosphonitrilic chloride trimer ("PNC") wherein each X in Formula I is chlorine. In tethering the PNC to a substrate, at least one of the chlorines is reacted with a moiety on the surface of a substrate to bond the PNC moiety to the substrate. When the PNC moiety is bonded to the substrate, the phosphonitrilic tethering compound includes additional reactive groups, each capable of reacting with a nucleophile-containing material, such as a biologically active material, to tether the biologically active material to the substrate through the phosphonitrilic moiety.

In some embodiments of the invention, the phosphonitrilic tethering groups may be derived solely from PNC molecules. In some embodiments, the phosphonitrilic tethering groups may be derived from compounds considered to be oligomers or derivatives of PNC. Referring to Formula I, tethering groups derived solely from PNC are those compounds of Formula I wherein each X is chlorine.

Oligomers of phosphonitrilic trimer suitable for use in the present invention include compounds of Formula I wherein at least one of the X groups is chlorine.

Derivatives of PNC suitable for inclusion in the phosphonitrilic tethering groups of the present invention include compounds of Formula I wherein at least one X is substituted with a moiety that may include monofunctional groups, difunctional groups or other multifunctional groups wherein the functional groups are typically nucleophiles. Such functional groups may be organic moieties that may be, in whole or in part, aliphatic (straight chain or branched chain) or aromatic. In some embodiments, the monofunctional, difunctional and/or multifunctional moieties may be bonded to a phosphonitrilic moiety prior to the attachment of the phosphonitrilic moiety to the substrate. In some embodiments, the monofunctional, difunctional and/or multifunctional moieties may be bonded to a phosphonitrilic moiety after the phosphonitrilic moiety has already been attached (e.g., bonded) to a substrate.

In embodiments where the phosphonitrilic moiety is derived from PNC, the reaction of the chlorines (X of Formula I are all chlorine) is typically sequential and the reactivity of each chlorine depends on the number of chlorines remaining on the PNC molecule, the nature of the moiety being reacted with the PNC (e.g., nucleophilicity, steric hindrance) and the reaction conditions (temperature, presence of water, stoichiometry or reactants, etc.). Where one of group X, for example, of Formula I is reacted with a moiety on the surface of a substrate to bond the phosphonitrilic moiety to the substrate, the remaining unreacted X groups remain capable of reacting with nucleophile-containing materials including monofunctional, difunctional and/or multifunctional moieties.

Monofunctional groups include moieties with a reactive group (e.g., nucleophiles) capable of reacting with one of the X groups of the compounds of Formula I but generally do not include additional reactive groups. In some embodiments, monofunctional groups may comprise groups having one or more desired properties that are needed or desired in the substrates or the tethering groups of the present invention. Suitable monofunctional groups include groups that render the reaction product hydrophilic or hydrophobic, groups that enhance solubility in certain solvents, groups that enhance molecular interactions, and the like. Examples include monofunctional organic alcohols, amines and mercaptans.

Difunctional groups may be linking groups in that they include a first reactive group that can react with a phosphonitrilic moiety and a second reactive group that can also react with the phosphonitrilic moiety or it can react with another compound or moiety including a second compound of Formula I such as PNC, for example. In some embodiments difunctional groups comprise linking groups that can link phosphonitrilic moieties to one another to form a tethering group comprised of at least two phosphonitrilic moieties connected to one another through the difunctional linking group. In such a configuration, the phosphonitrilic moieties will include unreacted groups (e.g., unreacted X groups according to Formula I) capable of bonding with other nucleophile-containing materials such biologically active molecules, for example. In some embodiments, the unreacted groups may comprise chlorines on one, two or more phosphonitrilic moieties tethered or linked together through one or more difunctional linking groups. In some embodiments, the difunctional groups can react with two reactive groups on the same phosphonitrilic moiety (two X groups of Formula I).

Suitable difunctional moieties include compounds having two reactive groups such as two nucleophilic groups. Some specific difunctional moieties include, for example, 4,7,10-trioxa-1,13-tridecane diamine, 1,6-hexanediamine, methyloxirane, p-phenylenediamine, 2-aminoethanol, 4,4-thiobis-benzenethiol, dimethyl-1,6-hexanediamine. Other difunctional moieties will be known to those of skill in the art, and the invention is not to be limited in any respect to the foregoing specific moieties.

Multifunctional moieties may also comprise linking groups in that they include a first reactive group that can react with a first phosphonitrilic moiety bonded to a substrate, and second, third and possibly other additional reactive groups that can react with the same phosphonitrilic moiety or other compounds or moieties including other phosphonitrilic moieties or compounds of Formula I (e.g., TCT). In some embodiments multifunctional groups include linking groups that can link two or more phosphonitrilic moieties to one another to form a branched tethering group comprised of two or more phosphonitrilic moieties linked together through the multifunctional linking group. In such a configuration, the phosphonitrilic moieties will include unreacted groups (e.g., unreacted X groups according to Formula I) capable of bonding with other nucleophile-containing materials such as one or more biologically active molecules, for example. In some embodiments, the unreacted groups may comprise chlorines on one, two or more phosphonitrilic moieties tethered or linked together through one or more multifunctional linking groups. In some embodiments, the multifunctional linking group may react with more than one reactive group on a first phosphonitrilic group and then may also react with other reactive groups on other phosphonitrilic groups or other groups.

Suitable multifunctional moieties include compounds having more than two reactive groups (e.g., nucleophilic groups). In some embodiments, the multifunctional moieties may be oligomeric or polymeric moieties. Some specific multifunctional moieties include, for example, hydrolyzed 2-ethyl-4,5-dihydro-oxazole homopolymer, polyethylenimine (including linear and branched configurations), as well as other moieties known to those of ordinary skill.

It will be understood that the foregoing description should not be interpreted as limited to the specific monofunctional, difunctional or other multifunctional groups described herein. The present invention is intended to encompass tethering compounds and tethering groups that include at least one phosphonitrilic moiety.

The invention provides articles that include a phosphonitrilic tethering group, as described herein, attached to a substrate. The substrate-attached tethering group is the reaction product of a complementary functional group "G" on a surface of a substrate with at least one of the X groups of compounds of Formula I. The substrate-attached tethering group has at least one, typically two or more reactive groups that can react with another molecule or materials (e.g., a nucleophile-containing material) to capture the material and tether it to the substrate.

The substrate is a solid phase material to which the phosphonitrilic tethering compounds can be attached. The substrate is not soluble in a solution or solvent that might be used when attaching a compound of Formula I to the surface of the substrate. Typically, a phosphonitrilic tethering compound is attached only to an outer portion of the substrate while the remaining portions of the substrate are not modified during the process of attaching phosphonitrilic tethering groups to the substrate. If the substrate has groups "G" distributed throughout the substrate, typically only those groups in the outer portion (e.g., on or near the surface) are usually capable of reacting with an X group of the compounds according to Formula I.

The substrates can have any useful form including, but not limited to, thin films, sheets, membranes, filters, nonwoven or woven fibers, hollow or solid beads, bottles, plates, tubes, rods, pipes, or wafers. The substrates can be porous or non-porous, rigid or flexible, transparent or opaque, clear or colored, and reflective or non-reflective. Suitable substrate materials include, for example, polymeric materials, glasses, ceramics, metals, metal oxides, hydrated metal oxides, or combinations thereof.

The substrates can be a single layer or material or can have multiple layers of one or more materials. For example, the substrate can have one or more inner or first layers that provide support for the outermost layer wherein the outer layer of the substrate includes a complementary functional group capable of reacting with the X group in compound of Formula I. In some embodiments, a surface of an outer layer may be chemically modified or coated with another material to provide an outer layer that includes a complementary functional group capable of reacting with a phosphonitrilic group including groups according to Formula I.

Suitable polymeric materials for use as a substrate or as a portion of a substrate include, but are not limited to, polyolefins, polystyrenes, polyacrylates, polymethacrylates, polyacrylonitriles, poly(vinylacetates), polyvinyl alcohols, polyvinyl chlorides, polyoxymethylenes, polycarbonates, polyamides, polyimides, polyurethanes, phenolics, polyamines, amino-epoxy resins, polyesters, silicones, cellulose based polymers, polysaccharides, or combinations thereof. In some embodiments, the polymeric material is a copolymer prepared using a co-monomer having a complementary functional group capable of reacting with a phosphonitrilic group including group X in compounds according to Formula I. For example, the co-monomer can contain a carboxy, mercapto, hydroxy, amino, or alkoxysilyl group.

In some embodiments, suitable polymeric materials include those resulting from thermally induced phase separation ("TIPS") which is a phase inversion method in which an initially homogeneous polymer solution is cast and exposed to a cooler interface (e.g., a water bath or chilled casting wheel), and phase separation is induced in the solution film by lowering the temperature. Suitable TIPS films or membranes may possess a broad range of physical film properties and microscopic pore sizes. They may be relatively rigid or non-rigid substrates prepared from any of a variety of polymers. TIPS membranes made according to the teachings of U.S. Pat. Nos. 4,539,256, 5,120,594, and 5,238,623 are all suitable for use in the invention. The TIPS membranes may comprise high density polyethylene (HDPE), polypropylene, polyvinylidenefluoride (PVDF), polyethylene-vinyl alcohol copolymer (e.g., available under the trade designation EVAL F101A from EVAL Company of America (EVALCA), Houston, Tex.), for example. The membrane may comprise a combination of materials such as a TIPS HDPE or a polypropylene membrane coated with a hydrophilic polymer (e.g., polyethylene-vinyl alcohol copolymer or EVAL) or a TIPS polypropylene support coated with a hydrophilic, strongly basic positively-charged coating such as polydiallyldimethylammonium chloride or a polymer incorporating quaternized dimethylaminoethylacrylate. Another example of a suitable TIPS membrane for use in the present invention is an HDPE membrane commercially available from 3M Company of St. Paul, Minn. Features of such a membrane include a pore size of about 0.09 um with a thickness of about 0.9 mil (0.023 mm). In general, the TIPS technology can provide a broad range of physical film properties having pore sizes in the micro- and ultrafiltration range such as those comprising a pore diameter within the range from about 80 nm to about 0.5 micrometer.

Combinations of materials may be used as a solid support member and the foregoing description is to be understood to include the aforementioned materials alone and in combination with other materials.

Some embodiments of the invention may utilize a multi-layered substrate having a diamond like glass (DLG) coating applied to a TIPS membrane or over another polymer substrate. The DLG coating may be applied using known techniques such as by a plasma deposition process according to that described in EP 1 266 045 B1 (David et al). In embodiments with a TIPS substrate, a DLG coating is typically applied over the entire surface of the TIPS membrane so that the DLG extends into the pores of the TIPS membrane. As mentioned, other materials may be used in the manufacture of a TIPS membrane, and a DLG coating may similarly be applied to such other materials in order to provide a suitable substrate for use in the present invention.

Suitable glass and ceramic substrate materials can include, for example, sodium, silicon, aluminum, lead, boron, phosphorous, zirconium, magnesium, calcium, arsenic; gallium, titanium, copper, or combinations thereof. Glasses typically include various types of silicate containing materials.

In some embodiments, the substrate includes a layer of diamond-like glass such as is described in International Patent Application WO 01/66820 A1, the disclosure of which is incorporated herein by reference in its entirety. The diamond-like glass is an amorphous material that includes carbon, silicon, and one or more elements selected from hydrogen, oxygen, fluorine, sulfur, titanium, or copper. Some diamond-like glass materials are formed from a tetramethylsilane precursor using a plasma process. A hydrophobic material can be produced that is further treated in an oxygen plasma to control the silanol concentration on the surface.

Diamond-like glass can be in the form of a thin film or in the form of a coating on another layer or material in the substrate. In some applications, the diamond-like glass can be in the form of a thin film having at least 30 weight percent carbon, at least 25 weight percent silicon, and up to 45 weight percent oxygen. Such films can be flexible and transparent. In some embodiments, the diamond-like glass is the outer layer of a multilayer substrate. In a specific example, the second layer (e.g., support layer) of the substrate is a polymeric material and the first layer is a thin film of diamond-like glass. The tethering group is attached to the surface of the diamond-like glass.

In some multilayer substrates, the diamond like glass is deposited on a layer of diamond-like carbon. For example, the second layer (e.g., support layer) is a polymeric film having a layer of diamond-like carbon deposited on a surface. A layer of diamond-like glass is deposited over the diamond-like carbon layer. In some embodiments, the diamond-like carbon is a tie layer or primer layer between a polymeric layer and a layer of diamond-like glass in a multilayer substrate. For example, the multilayer substrate can include a polyimide or polyester layer, a layer of diamond-like carbon deposited on the polyimide or polyester, and a layer of diamond-like glass deposited on the diamond-like carbon. In another example, the multilayer substrate includes a stack of the layers arranged in the following order: diamond-like glass, diamond-like carbon, polyimide or polyester, diamond-like carbon, and diamond-like glass.

Diamond-like carbon films can be prepared, for example, from acetylene in a plasma reactor. Other methods of preparing such films are described U.S. Pat. Nos. 5,888,594 and 5,948,166 as well as in the article M. David et al., *AlChE Journal*, 37 (3), 367-376 (March 1991), the disclosures of which are incorporated herein by reference.

Suitable metals, metal oxides, or hydrated metal oxides for substrates can include, for example, gold, silver, platinum, palladium, aluminum, copper, chromium, iron, cobalt, nickel, zinc, and the like. The metal-containing material can be alloys such as stainless steel, indium tin oxide, and the like. In some embodiments, a metal-containing material is the top layer of a multilayer substrate. For example, the substrate can have a polymeric second layer and a metal containing first layer. In one example, the second layer is a polymeric film and the first layer is a thin film of gold. In other examples, a multilayer substrate includes a polymeric film coated with a titanium-containing layer and then coated with a gold-containing layer. That is, the titanium layer can function as a tie layer or a primer layer for adhering the layer of gold to the polymeric film.

In other examples of a multilayer substrate, a silicon support layer is covered with a layer of chromium and then with a layer of gold. The chromium layer can improve the adhesion of the gold layer to the silicon layer.

The surface of the substrate typically includes a group capable of reacting with a carboxy, halogen (e.g., chlorine), halocarbonyl, halocarbonyloxy, cyano, hydroxy, mercapto, isocyanato, halosilyl, alkoxysilyl, acyloxysilyl, azido, haloalkyl, tertiary amino, primary aromatic amino, secondary aromatic amino, disulfide, alkyl disulfide, benzotriazolyl, phosphonitrilic, phosphono, phosphoroamido, phosphato, or ethylenically unsaturated group. That is, the substrate includes a group "G" capable of reacting with the group X in compounds of Formula I (i.e., the substrate includes a complementary functional group to the group X). Substrates can include a support material that is treated to have an outer layer that includes a complementary functional group. The substrate can be prepared from any solid phase material known to have groups capable of reacting with X or which is capable of reacting with an intermediate compound that can act as a linking group by reacting with a moiety on the surface of the substrate and with X to link the substrate and the phosphonitrilic group together.

A carboxy group or a halocarbonyl group can react with a substrate having a hydroxy group to form a carbonyloxy-containing attachment group. Examples of substrate materials having hydroxy groups include, but are not limited to, polyvinyl alcohol, corona-treated polyethylene, hydroxy substituted esters of polymethacrylates, hydroxy substituted esters of polyacrylates, and a polyvinyl alcohol coating on a support material such as glass or polymer film.

A carboxy group or a halocarbon group can also react with a substrate having a mercapto group to form a carbonylthio-containing attachment group. Examples of substrate materials having a mercapto group include, but are not limited to, mercapto substituted esters of polyacrylates, mercapto substituted esters of polymethacrylates, and glass treated with a mercaptoalkylsilane.

Additionally, a carboxy group or a halocarbonyl group can react with a primary aromatic amino group, a secondary aromatic amino group, or a secondary aliphatic amino group to form a carbonylimino-containing attachment group. Examples of substrate materials having aromatic primary or secondary amino groups include, but are not limited to, polyamines, amine substituted esters of polymethacrylate, amine substituted esters of polyacrylate, polyethylenimines, and glass treated with an aminoalkylsilane.

A halocarbonyloxy group can react with a substrate having a hydroxy group to form an oxycarbonyloxy-containing attachment group. Examples of substrate materials having hydroxy groups include, but are not limited to, polyvinyl alcohol, corona-treated polyethylene, hydroxy substituted esters of polymethacrylates, hydroxy substituted esters of polyacrylates, and a polyvinyl alcohol coating on a support material such as glass or polymer film.

A halocarbonyloxy group can also react with a substrate having a mercapto group to form an oxycarbonylthio-containing attachment group. Examples of substrate materials having a mercapto group include, but are not limited to, mercapto substituted esters of polymethacrylates, mercapto substituted esters of polyacrylates, and glass treated with a mercaptoalkylsilane.

Additionally, a halocarbonyloxy group can react with a substrate having a primary aromatic amino group, a secondary aromatic amino group, or a secondary aliphatic amino group to form an oxycarbonylimino-containing attachment group. Examples of substrate materials having aromatic primary or secondary amino groups include, but are not limited to, polyamines, amine substituted esters of polymethacrylate, amine substituted esters of polyacrylate, polyethylenimines, and glass treated with an aminoalkylsilane.

A hydroxy group can react with a substrate having isocyanate group to form an oxycarbonylimino-containing attachment group. Suitable substrates having isocyanate groups include, but are not limited to, a coating of 2-isocyanatoethylmethacrylate polymer on a support material. Suitable support materials include glass and polymeric materials such as polyesters, polyimides, and the like.

A hydroxy group can also react with a substrate having a carboxy, carbonyloxycarbonyl, or halocarbonyl to form a carbonyloxy-containing attachment group. Suitable substrates include, but are not limited to, a coating of acrylic acid polymer or copolymer on a support material or a coating of a methacrylic acid polymer or copolymer on a support material. Suitable support materials include glass and polymeric materials such as polyesters, polyimides, and the like. Other suitable substrates include copolymers of polyethylene with polyacrylic acid, polymethacrylic acid, or combinations thereof.

A mercapto group can react with a substrate having isocyanate groups. The reaction between a mercapto group and an isocyanate group forms a thiocarbonylimino-containing attachment group. Suitable substrates having isocyanate groups include, but are not limited to, a coating of 2-isocyanatoethylmethacrylate copolymer on a support material. Suitable support materials include glass and polymeric materials such as polyesters, polyimides, and the like.

A mercapto group can also react with a substrate having a halocarbonyl group to form a carbonylthio-containing attachment group. Substrates having halocarbonyl groups include, for example, chlorocarbonyl substituted polyethylene.

A mercapto group can also react with a substrate having a halocarbonyloxy group to form an oxycarbonlythio-containing attachment group. Substrates having halocarbonyl groups include chloroformyl esters of polyvinyl alcohol.

Additionally, a mercapto group can react with a substrate having an ethylenically unsaturated group to form a thioether-containing attachment group. Suitable substrates having an ethylenically unsaturated group include, but are not limited to, polymers and copolymers derived from butadiene.

A phosphonitrilic moiety such as PNC can react with nucleophile-containing materials including glass, diamond-like glass, metal, metal oxide and polymeric substrates with nucleophile functionality. DLG surfaces may be treated to comprise a surface comprising a nucleophile such as an aminosilane (e.g., 3-aminopropyl triethoxysilane, 3-amino trimethoxy silane) that will provide the necessary functionality to react with a PNC moiety. Such a surface my also comprise a porous polymeric coating (e.g., TIPS materials described herein). Polymeric substrates can also include, for example, ammonia grafted sintered polyethylene, aminated polyester blown melt fiber membrane, hydroxylated polypropylene, polyester, and polyethylene blown melt fiber membrane, and aminomethylated styrene divinylbenzene. PNC materials may also be reacted with metal or metal oxide materials.

An isocyanate group can react with a substrate having a hydroxy group to form a oxycarbonylimino-containing attachment group. Examples of substrate materials having hydroxy groups include, but are not limited to, polyvinyl alcohol, corona-treated polyethylene, hydroxy substituted esters of polymethacrylates or polyacrylates, and a polyvinyl alcohol coating on glass or polymer film.

An isocyanate group can also react with a mercapto group to form a thiocarbonylimino-containing attachment group. Examples of substrate materials having a mercapto group include, but are not limited to, mercapto substituted esters of polymethacrylates or polyacrylates and glass treated with a mercaptoalkylsilane.

Additionally, an isocyanate group can react with a primary aromatic amino group, a secondary aromatic amino group, or a secondary aliphatic amino group to form a urea-containing attachment group. Suitable substrates having a primary or secondary aromatic amino group include, but are not limited to, polyamines, polyethylenimines, and coatings of an aminoalkylsilane on a support material such as glass or on a polymeric material such as a polyester or polyimide.

An isocyanate group can also react with a carboxy to form an O-acyl carbamoyl-containing attachment group. Suitable substrates having a carboxylic acid group include, but are not limited to, a coating of an acrylic acid polymer or copolymer or a coating of a methacrylic acid polymer or copolymer on a glass or polymeric support. Copolymers include, but are not limited to, copolymers that contain polyethylene and polyacrylic acid or polymethacrylic acid. Suitable polymeric support materials include polyesters, polyimides, and the like.

A halosilyl group, an alkoxysilyl group, or an acyloxysilyl group can react with a substrate having a silanol group to form a disiloxane-containing attachment group. Suitable substrates include those prepared from various glasses, ceramic materials, or polymeric material. These groups can also react with various materials having metal hydroxide groups on the surface to form a silane-containing linkage. Suitable metals include, but are not limited to, silver, aluminum, copper, chromium, iron, cobalt, nickel, zinc, and the like. In some embodiments, the metal is stainless steel or another alloy. Polymeric material can be prepared to have silanol groups. For example, commercially available monomers with silanol groups include 3-(trimethoxysilyl)propyl methacrylate and 3-aminoproplytrimethoxysilane available from Aldrich Chemical Co., Milwaukee, Wis.

An azido group can react, for example, with a substrate having carbon-carbon triple bond to form triazolediyl-containing attachment groups. An azido group can also react with a substrate having nitrile groups to form a tetrazenediyl-containing attachment group. Substrates having nitrile groups include, but are not limited to, coatings of polyacrylonitrile on a support material such as glass or a polymeric material. Suitable polymeric support material includes polyesters and polyimides, for example. Other suitable substrates having nitrile groups include acrylonitrile polymers or copolymers and 2-cyanoacrylate polymers or copolymers.

An azido group can also react with a strained olefinic group to form a triazolediyl-containing attachment group. Suitable substrates have a strained olefinic group include coatings that have pendant norbornenyl functional groups. Suitable support materials include, but are not limited to, glass and polymeric materials such as polyesters and polyimides.

An aziridinyl group can react with a mercapto group to form a aminoalkylthioether-containing attachment group. Examples of substrate materials having a mercapto group include, but are not limited to, mercapto substituted esters of poly methacrylates or polyacrylates and glass treated with a mercaptoalkylsilane.

Additionally, an aziridinyl group can react with a carboxy group to form a β-aminoalkyloxycarbonyl-containing attachment group. Suitable substrates having a carboxy include, but are not limited to, a coating of a acrylic acid polymer or copolymer, or a coating of a methacrylic acid polymer or copolymer on a glass or polymeric support. Copolymers include, but are not limited to, copolymers that contain polyethylene and polyacrylic acid or polymethacrylic acid. Suitable polymeric support materials include polyesters, polyimides, and the like.

A haloalkyl group can react, for example, with a substrate having a tertiary amino group to form a quaternary ammonium-containing attachment group. Suitable substrates having a tertiary amino group include, but are not limited to, polydimethylaminostyrene or polydimethylaminoethylmethacrylate.

Likewise, a tertiary amino group can react, for example, with a substrate having a haloalkyl group to form a quaternary ammonium-containing attachment group. Suitable substrates having a haloalkyl group include, for example, coatings of a haloalkylsilane on a support material. Support materials can include, but are not limited to, glass and polymeric materials such as polyesters and polyimides.

A primary aromatic amino or a secondary aromatic amino group can react, for example, with a substrate having an isocyanate group to form a oxycarbonylimino-containing attachment group. Suitable substrates having isocyanate groups include, but are not limited to, a coating of a 2-isocyanatoethylmethacrylate polymer or copolymer on a glass or polymeric support. Suitable polymeric supports include polyesters, polyimides, and the like.

A primary aromatic amino or a secondary aromatic amino group can also react with a substrate containing a carboxy or halocarbonyl group to form a carbonylimino-containing attachment group. Suitable substrates include, but are not limited to, acrylic or methacrylic acid polymeric coatings on a support material. The support material can be, for example, glass or a polymeric material such as polyesters or polyimides. Other suitable substrates include copolymers of polyethylene and polymethacrylic acid or polyacrylic acid.

A disulfide or an alkyl disulfide group can react, for example, with a metal surface to form a metal sulfide-containing attachment group. Suitable metals include, but are not limited to gold, platinum, palladium, nickel, copper, and chromium. The substrate can also be an alloy such an indium tin oxide or a dielectric material.

A benzotriazolyl can react, for example, with a substrate having a metal or metal oxide surface. Suitable metals or metal oxides include, for example, silver, aluminum, copper, chromium, iron, cobalt, nickel, zinc, and the like. The metals or metal oxides can include alloys such as stainless steel, indium tin oxide, and the like.

A phosphonitrilic can react with a substrate having amino functionality associated with the surface of the substrate. Glass surfaces and diamond-like glass surfaces treated with an aminosilane are suitable for reacting with and attaching to a phosphonitrilic moiety. In a such a DLG substrate, the amino functionality provides a complementary functional group "G" capable of reacting with an X group (e.g., chlorine) on the phosphonitrilic moiety by nucleophilic attack. In the resulting system, the X group is replaced by the amino functionality, thus tethering the phosphonitrilic moiety to the substrate.

A phosphono, phosphoroamido, or phosphato can react, for example, with a substrate having a metal or metal oxide surface. Suitable metals or metal oxides include, for example, silver, aluminum, copper, chromium, iron, cobalt, nickel, zinc, and the like. The metals or metal oxides can include alloys such as stainless steel, indium tin oxide, and the like.

An ethylenically unsaturated group can react, for example, with a substrate having an alkyl group substituted with a mercapto group. The reaction forms a heteroalkylene-containing attachment group. Suitable substrates include, for example, mercapto-substituted alkyl esters of polyacrylates or polymethacrylates.

An ethylenically unsaturated group can also react with a substrate having a silicon surface, such as a silicon substrate formed using a chemical vapor deposition process. Such silicon surfaces can contain —SiH groups that can react with the ethylenically unsaturated group in the presence of a platinum catalyst to form an attachment group with silicon bonded to an alkylene group.

Additionally, an ethylenically unsaturated group can react with a substrate having a carbon-carbon double bond to form an alkylene-containing attachment group. Such substrates include, for example, polymers derived from butadiene.

Articles according to the invention typically include a substrate and a substrate-attached tethering group that includes a reaction product of a complementary substrate-functional group on a surface of the substrate with a phosphonitrilic compound of Formula I (e.g., PNC) where the substrate-attached functional group is a group capable of reacting with X to form an ionic bond, a covalent bond, or combinations thereof. In some embodiments, a single complementary substrate functional group may react to form more than one bond with a single phosphonitrilic compound. Unreacted groups on the substrate-attached functional group (e.g., unreacted chloride) are available for further reaction with nucleophile-containing materials.

More than one phosphonitrilic tethering group is typically attached to the substrate if there are more than one reactive group on the substrate. Further, the substrate can have excess reactive groups on the surface of the substrate that have not reacted with a phosphonitrilic tethering compound.

Groups on a substrate that are capable of reacting with the phosphonitrilic tethering compound include, but are not limited to, hydroxy, mercapto, primary aromatic amino group, secondary aromatic amino group, secondary aliphatic amino group, aminosilane, azido, carboxy, carbonyloxycarbonyl, isocyanate, halocarbonyl, halocarbonyloxy, silanol, and nitrile.

The attachment of tethering compounds to the surface of a substrate (i.e., formation) can be detected using techniques such as, for example, contact angle measurements of a liquid on the substrate before and after attachment of a phosphonitrilic tethering compound (e.g., the contact angle can change upon attachment of a tethering group to the surface of a substrate), ellipsometry (e.g., the thickness of the attached layer can be measured), time-of-flight mass spectroscopy (e.g., the surface concentration can change upon attachment of a tethering group to a substrate), and Fourier Transform Infrared Spectroscopy (e.g., the reflectance and absorbance can change upon attachment of a tethering group to a substrate).

In some embodiments of articles of the invention, a halogen-containing moiety in the phosphonitrilic tethering group is reacted with an amine-containing material resulting in the immobilization of an amine-containing material to the substrate. In some embodiments, the amine-containing materials are biomolecules such as, for example, amino acid, peptide, DNA, RNA, protein, enzyme, organelle, immunoglobin, or fragments thereof. In other embodiments, the amine-containing material is a non-biological amine such as an amine-containing analyte. The presence of the immobilized amine can be determined, for example, using mass spectroscopy, contact angle measurement, infrared spectroscopy, and ellipsometry. Additionally, various immunoassays and optical microscopic techniques can be used if the amine-containing material is a biologically active material.

Other materials can be bound to the amine-containing material. For example, a complementary RNA or DNA fragment can hybridize with an immobilized RNA or DNA fragment. In another example, an antigen can bind to an immobilized antibody or an antibody can bind to an immobilized antigen. In a more specific example, a bacterium such as *Staphylococcus aureus* can bind to an immobilized biomolecule.

Another aspect of the invention provides methods for immobilizing a nucleophile-containing material to a substrate. The method involves preparing a substrate-attached tethering group by reacting a complementary functional group on the surface of the substrate with a phosphonitrilic moiety (e.g., reacting at least one of the reactive groups X in compounds of Formula I); and reacting at least one reactive group of the phosphonitrilic moiety (e.g., one or more of the remaining reactive groups X of Formula I) with a nucleophile-containing material to form a phosphonitrilic connector group between the substrate and the nucleophile-containing material. In one embodiment, the nucleophile-containing material is an amine-containing material and the method of immobilizing the amine-containing material is represented in Reaction Scheme A:

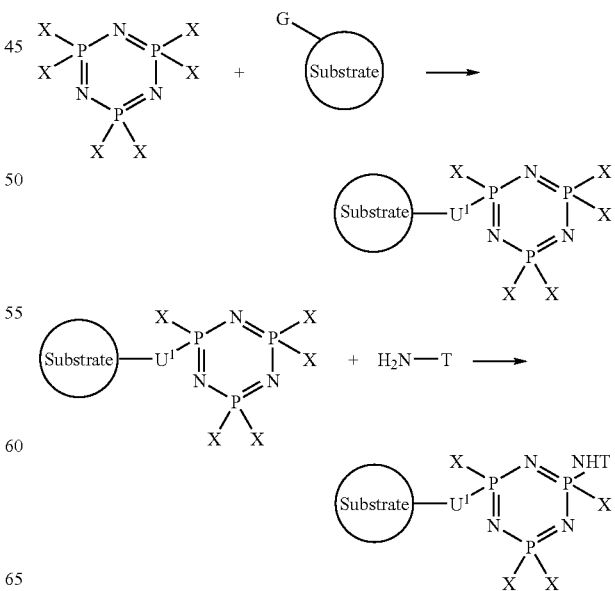

where $U^1$ is the attachment group formed by reacting one X group in a compound of Formula I with a complementary functional group G on the surface of the substrate; T is the remainder of the amine-containing material (e.g., the group T represents all of the amine-containing material exclusive of the amine group). $H_2N$-T is any suitable amine-containing material. In some embodiments, $H_2N$-T is a biomolecule.

Variations of the foregoing Reaction Scheme A are also within the scope of the invention. In embodiments where monofunctional moieties are bonded to a phosphonitrilic moiety, methods involve preparing a substrate-attached tethering group by reacting a complementary functional group on the surface of the substrate with the phosphonitrilic group (e.g., at least one of the reactive groups X in compounds of Formula I), and reacting the phosphonitrilic group (e.g., another of the remaining reactive groups X of Formula I) with one or more monofunctional moieties to form a tethering group that includes a phosphonitrilic moiety bonded to a substrate with a monofunctional moiety also bonded to the phosphonitrilic moiety. A nucleophile-containing material may be bonded to the phosphonitrilic moiety to tether the nucleophile containing material to the substrate.

In embodiments having a difunctional moiety, the difunctional moiety is bonded to a first phosphonitrilic moiety that is tethered to the surface of a substrate. The difunctional moiety may also be bonded to a second phosphonitrilic moiety, and the second phosphonitrilic moiety may be bonded to a nucleophile-containing material to tether the nucleophile-containing material to the substrate. In embodiments comprising multifunctional moieties, the multifunctional moiety may be bonded to a first phosphonitrilic moiety that is tethered to the surface of a substrate and the multifunctional moiety may also be bonded to a second, third, or other additional phosphonitrilic moieties. In turn, reactive groups on the first, second, third or other phosphonitrilic moiety may react with and bond to a nucleophile-containing material to tether the nucleophile-containing material to the substrate. Additionally, multifunctional moieties may react with multiple reactive groups on single phosphonitrilic groups.

Accordingly, a method of immobilizing a nucleophile-containing material to a substrate is provided, the method involving:

Providing a phosphonitrilic tethering compound (e.g., a compound according to Formula I);

Providing a substrate having a complementary functional group capable of reacting with a phosphonitrilic tethering compound;

Preparing a substrate-attached phosphonitrilic tethering group by reacting the phosphonitrilic tethering compound with the complementary functional group on the substrate resulting in an ionic bond, covalent bond, or combinations thereof, and Reacting the substrate-attached phosphonitrilic tethering group with a nucleophile-containing material to immobilize the nucleophile-containing material.

The compounds of the invention can be used, for example, for immobilizing nucleophile-containing material such as an amine-containing material. In some embodiments, the amine-containing material is an amine-containing analyte. In other embodiments, the amine-containing materials are biomolecules such as, for example, amino acids, peptides, DNA, RNA, protein, enzymes, organelles, immunoglobins, or fragments thereof. Immobilized biological amine-containing materials can be useful in the medical diagnosis of a disease or of a genetic defect. The immobilized amine-containing materials can also be used for biological separations or for detection of the presence of various biomolecules. Additionally, the immobilized amine-containing materials can be used in bioreactors or as biocatalysts to prepare other materials. The substrate-attached tethering groups can be used to detect amine-containing analytes.

Biological amine-containing materials often can remain active after attachment to the substrate so that an immobilized antibody can bind with antigen or an immobilized antigen can bind to an antibody. An amine-containing material can bind to a bacterium. In a more specific example, the immobilized amine-containing material can bind to a *Staphylococcus aureus* bacterium (e.g., the immobilized amine-containing material can be a biomolecule that has a portion that can specifically bind to the bacterium).

The embodiments of the invention are further described in the following non-limiting Examples.

EXAMPLES

Example 1

A functionalized porous membrane coated with diamond-like glass (DLG) was prepared. A 5 cm² high density polyethylene thermally induced phase separation (HDPE TIPS) membrane (obtained from 3M Company, St. Paul, Minn.) with a pore size of about 0.09 um and having a thickness of about 23 micrometers was diamond like glass (DLG) coated, using a plasma process as described in EP 1 266 045 B1 (David et al) to extend the DLG coating into the pores of the TIPS membrane. The DLG-coated TIPS membrane was placed in 50 ml of ethanol containing 2% by volume 3-amino propyl triethoxy silane (Sigma-Aldrich, St. Louis, Mo.), 1 ml water and few drops of 0.1N acetic acid. After 10 minutes in this solution the membrane was removed and washed with ethanol and dried.

A PNC trimer was tethered on the functionalized membrane by placing the membrane in 20 ml of a toluene solution containing 0.2 g of PNC (Sigma Aldrich, St. Louis, Mo.) which was purified by sublimation. The amino group of the aminosilane was reacted with the phosphazene ring by displacing a chlorine, leaving the remaining chlorines available for attachment to a biologically active molecule such as a protein molecule. The membrane was placed in a solution of glucose oxidase containing 10 mg glucose oxidase in PBS buffer solution for 3 hours. The membrane was removed and washed with water and buffer solution followed by washes with sodium dodecylsulfate to remove any ionically bound proteins.

Bicinchonic acid analysis (BCA) was performed on the membrane from Example 1 using a commercial protein assay kit and procedure (Pierce Chemicals, Rockford, Ill.) to determine the total amount of protein that had been immobilized on the surface. The amount of total protein immobilized in a 1 cm² TIPS porous membrane was determined to be 212 µg/1.5 mg of membrane.

A glucose oxidase assay was performed to determine the amount of enzyme that was active in the membrane. The assay utilized a glucose oxidase assay kit using a procedure obtained from Sigma-Aldrich. The amount of enzyme active was initially determined to be 25.5 µg/1.5 mg of membrane. After five (5) days, the amount of enzyme active was 23.3 µg/1.5 mg of membrane.

An experiment was conducted to demonstrate that the enzyme activity is attributable to the covalent attachment of the enzyme to tethering groups on the surface of the membrane and not from the unattached enzyme in solution. A 1 cm² substrate, prepared as described above, was placed in the glucose oxidase assay solution for 30 seconds and the absorbance at 450 nm was measured. The membrane was then removed from the solution for about 30 seconds and the absorbance was checked again. No increase in absorbance was noted for the membrane after it was removed from solution, thus indicating a lack of free floating enzyme. The membrane was placed back into the solution to allow further reaction to take place between the enzymes in solution and the tethering groups on the surface of the substrate. Additional absorbance measurements were collected for 60 minutes, and the data is summarized in Table 1.

TABLE 1

Absorbance at 450 nm

| Time (min) | Absorbance (nm) |
|---|---|
| 0 | 0 |
| 10 | 0.31979 |
| 20 | 0.36018 |
| 30 | 0.47089 |
| 40 | 0.49865 |
| 50 | 0.62823 |
| 60 | 0.64694 |

Example 2

Glass slides were treated with DLG using the following conditions. Each glass slide was etched in oxygen plasma for 10 seconds and exposed to a mixture of tetramethylsilane and oxygen plasma for 20 seconds followed by oxygen plasma for another 10 seconds. The DLG coated glass slides were then placed in a 1% solution of 3-aminopropyltriethoxy silane in ethanol for 10 minutes. Thereafter, the glass slides were removed and washed with ethanol and dried under a nitrogen flow. The dried glass slides were reacted with phosphoric chloride in toluene (Sigma Aldrich, St. Louis, Mo.). The reaction time was varied from several minutes up to one hour. Contact angle measurements were taken to monitor and confirm attachment of the PNC to the aminopropyltriethoxy silane attached to the DLG substrate. The amine has a low contact angle of 20 degrees, which on reaction with PNC increases to 45 degrees and which stabilized in about 10 minutes. Contact angle data for the attachment of the PNC is provided in Table 2.

TABLE 2

| Time (min) | Contact angle |
|---|---|
| 0 | 19.3 |
| 1 | 22.3 |
| 5 | 45.3 |
| 20 | 44.3 |
| 30 | 47.3 |
| 60 | 46.6 |

The sample with a 10 minute reaction time was further reacted with lysine by exposing the sample to a 1 mM solution of lysine (Sigma Aldrich). The reaction of the amino group of lysine to the PNC resulted in a decreased contact angle which stabilized within about 10 minutes following contact between the DLG coated slide and the lysine. Contact angle data is set forth in Table 3.

TABLE 3

| Time (min) | Contact angle |
|---|---|
| 0 | 55.2 |
| 1 | 27 |
| 5 | 15.5 |
| 20 | 15.3 |
| 30 | 19.3 |
| 60 | 15.7 |

Example 3

An approximately 20 cm by 30 cm polyimide film (obtained from E. I. du Pont de Nemours & Co., Wilmington, Del. under the trade designation "KAPTON E") was first coated with diamond-like carbon (DLC) followed by diamond-like glass (DLG). The polyimide film was affixed to the powered electrode of a Model 2480 parallel-plate capacitively coupled reactive ion etcher (Plasma Therm, St. Petersburg, Fla.) using 3M 811 adhesive tape (3M Company, St. Paul, Minn.). DLC was deposited onto the polyimide membrane using an acetylene plasma. The ion etcher chamber was closed and the chamber was pumped to a pressure of 0.67 Pa (0.005 Torr). Oxygen gas was introduced into the chamber at a flow rate of 500 standard $cm^3$ per minute, and the pressure of the chamber was maintained at 6.7 Pa (0.050 Torr). Plasma was ignited and was sustained at a power of 2000 W for 15 seconds. The oxygen gas flow was then terminated and the chamber was allowed to pump to a pressure of 0.67 Pa (0.005 Torr). Acetylene gas was introduced into the chamber at a flow rate of 200 standard $cm^3$ per minute, and the pressure of the chamber was maintained at 2 Pa (0.015 Torr). Plasma was ignited and was sustained at a power of 1600 W for 10 seconds. The flow of acetylene gas was then terminated and the chamber was allowed to pump to a pressure of 0.67 Pa (0.005 Torr).

Diamond-like glass (DLG) was thereafter deposited onto the DLC/polyimide substrate using a tetramethylsilane plasma by first introducing oxygen gas into the chamber at a flow rate of 500 standard $cm^3$ per minute. The pressure of the chamber was maintained at 20 Pa (0.15 Torr). Plasma was ignited and was sustained at a power of 300W for 10 seconds. With the oxygen flow rate maintained at 500 standard $cm^3$ per minute, tetramethylsilane gas was introduced into the chamber at a flow rate of 150 standard $cm^3$ per minute. The chamber pressure was maintained at 20 Pa (0.15 Torr). Plasma was ignited and was sustained at a power of 300 W for 12 seconds. The flow of tetramethylsilane gas was terminated. After a period of 1 minute, with both the flow of oxygen gas and the chamber pressure of 20 Pa (0.15 Torr) maintained, plasma was ignited and was sustained at a power of 300W for 20 seconds. The flow of oxygen gas was then terminated and the chamber pressure was allowed to pump to a pressure of 0.67 Pa (0.005 Torr). The chamber was then opened to the atmosphere and the polyimide/DLC/DLG substrate was repositioned so that the DLG coating faced the electrode. The foregoing sequence of plasma treatments was repeated to provide a substrate with polyimide having DLC/DLG coatings on both sides.

Two test substrates, each measuring about 1 $cm^2$, were cut from the 20 cm×30 cm polyimide/DLC/DLG substrate prepared according to the foregoing process. One of the substrates was designated as a control. The other substrate was designated as an experimental substrate, and the experimental substrate was further treated with 3-amino propyl triethoxy silane (Sigma-Aldrich, St. Louis, Mo.) and a PNC trimer as in Example 1. The control substrate was not treated and remained free of silane as well as PNC.

Mouse IgG against human (mIgG) was immobilized onto the DLG surface of the control substrate and the PNC treated surface of the experimental substrate by placing each substrate in a sterile culture tube and exposing the substrate to 1 ml of 100 mM CHES 2-{N-cyclohexylaminoethane} sulfonic acid buffer (commercially obtained from Sigma, St. Louis, Mo. under the catalog number C-2885), adjusted pH to 9, containing 50 µg of mIgG (commercially obtained from Jackson Immuno Research laboratories Inc West Grove, Pa., under catalog #209-005-082). The immobilization time for general assays was set to be two (2) hours while placed in a shaker (IKA HS 260 basic) at 120 motions/min at room temperature. The solution was removed from the culture tube by Pasteur pipette and the thus treated control and experimental substrates were washed three times with Phosphate buffered saline (PBS) buffer containing 0.05% Tween 20. Both of the substrates were again placed in sterile culture tubes and 1.5 ml of blocking buffer, PBS buffer containing 2% non-fat milk powder, was added to each of the culture tubes and allowed to react for one (1) hour while on the shaker. The solution was removed from the tubes with a Pasteur pipette and each of the substrates were again washed three times with the forgoing wash buffer.

The mIgG antibody was reacted with biotin-conjugated human IgG (hIgG-BT). The concentration of the hIgG-BT was 4 µg/ml (obtained from Jackson Immuno Research laboratories Inc West Grove, Pa., under catalog, #009-060-003) in PBS buffer. A volume of 1 ml of the solution was placed in the culture tube containing the substrate and incubated for one (1) hour in the shaker, and the substrates were then washed 3 times with buffer as previously described. This reaction was followed by reaction with streptavidin horse radish peroxide (SA-HRP), a detection enzyme that specifically binds to biotin. A volume of 1 ml of 0.5 µg/ml of SA-HRP (commercially obtained from Jackson Immuno Research laboratories Inc West Grove, Pa., under Catalog #023-060-021 in pH 7.4 buffer) was added to the culture tube and allowed to react for 30 minutes on a shaker. The samples were again washed 3 times with wash buffer, and a 1 ml volume of the coloring agent 2,2-azino-di(3-ethylbenzthiazoline) sulfonic acid (ABTS) at a concentration of 0.3 mg/ml was added to the culture tube to promote an enzymatic color change that could be measured at 405 nm on a spectrometer. After a 5 minute exposure to the ABTS, 1 ml of 1% Sodium Dodecyl sulfate (SDS) solution was added to stop the reaction.

Absorbance was measured for both the treated control substrate and for the treated experimental substrate using a UV-Vis spectrophotometer at 405 nm. Absorbance for the sample on the control was: 0.1. Absorbance for the sample on the experimental substrate was: 0.2

Example 4

1 cm² substrate (polyimide/DLC/DLG) samples were prepared and functionalized with silane and PNC as described in Example 3. Polyimide/DLC/DLG substrate with no silane or PNC treatment were used as 'control' substrates. Rabbit IgG specific to Staphylococcus Aureus (commercially obtained from Accurate Chemical and Scientific, Westbury, New York) in a 4.52 mg/ml solution was immobilized on the surface of the substrates, including the control substrate. The substrates were then fixed (by taping) on a glass plate and 50 µl of PBS buffer containing Staphylococcus aureus at a concentration of 5×10⁸ cfu/ml was added by pipetting the solution and allowing it to stand for approximately 30 minutes. The samples were washed and then stained by exposing each of the samples to acridine orange for 10 minutes. The acridine orange (obtained from Molecular probes under the designation A3568) was diluted with distilled water from a concentration of 10 mg/ml to 0.1 mg/ml prior to use.

Each of the thus stained substrates were viewed through a Olympus Model FV-300 confocal microscope (Leeds Precision, Inc, of Minnesota). The PNC functionalized substrates were observed to include a higher level of stained bacteria when compared with the non-functionalized control substrates, indicating the PNC functionalized substrates bound more of the S. aureus bacteria compared to the non-functionalized control samples.

What is claimed is:

1. An article comprising:
   a substrate having a first surface and a second surface, the first surface comprising a functional group;
   a phosphonitrilic tethering group ionically or covalently bonded to the first surface of the substrate, the phosphonitrilic tethering group comprising a reaction product of the functional group on the first surface of the substrate with a phosphonitrilic moiety;
   wherein the substrate comprises metal or metal oxide.

2. The article according to claim 1, wherein the substrate comprises metal or metal oxide selected from the group consisting of gold, silver, titanium, platinum, palladium, aluminum, copper, chromium, iron, cobalt, nickel, zinc, stainless steel, indium tin oxide, and combinations of two or more of the foregoing.

3. The article according to claim 1, wherein the substrate further comprises a support layer supporting the metal or metal oxide.

4. The article according to claim 3, wherein the support layer comprises a polymer.

5. The article according to claim 1 wherein the phosphonitrilic tethering compound comprises a structure according to Formula I

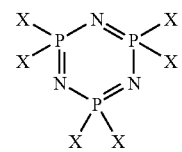

wherein each X may be the same or different and comprise reactive groups susceptible to nucleophilic attack to bond with a nucleophile-containing material.

6. The article according to claim 5 wherein each X is chlorine.

7. The article according to claim 1 further comprising a monofunctional, difunctional, or multifunctional moiety affixed to the phosphonitrilic tethering group.

* * * * *

UNITED STATES PATENT AND TRADEMARK OFFICE
CERTIFICATE OF CORRECTION

PATENT NO. : 7,658,994 B2
APPLICATION NO. : 10/896392
DATED : February 9, 2010
INVENTOR(S) : Lakshmi It is certified that error appears in the above-identified patent and that said Letters Patent is hereby corrected as shown below:

Title Page 1, Column 2
Line 7, under "Foreign Patent Documents," delete "WO01/66820" and insert -- WO 01/66820 --, therefor.
Line 8, under "Foreign Patent Documents," delete "WO03/050237" and insert -- WO 03/050237 --, therefor.

Title Page 2, Column 2
Line 8, under "Other Publications," delete "Scham" and insert -- Scharn --, therefor.

Column 1
Line 27, delete "NH2," and insert -- $NH_2$, --, therefor.

Column 3
Lines 30-31, delete "trimethoxy silane." and insert -- trimethoxysilane. --, therefor.

Column 5
Line 2, delete "azo-dystuffs," and insert -- azo-dyestuffs, --, therefor.
Line 3, delete "dystuffs," and insert -- dyestuffs, --, therefor.
Line 9, delete "OCH2" and insert -- $OCH_2$; --, therefor.

Column 11
Line 50, delete "halocarbon" and insert -- halocarbonyl --, therefor.

Column 14
Line 6, delete "aminoalkylthioether" and insert -- β-aminoalkylthioether --, therefor.
Line 9, delete "poly methacrylates" and insert -- polymethacrylates --, therefor.

Column 16
Line 56, delete "H₂N—T" and insert -- $H_2N$-T --, therefor.

Signed and Sealed this

Twenty-fourth Day of August, 2010

David J. Kappos
*Director of the United States Patent and Trademark Office*

Column 17
Line 52, delete "thereof," and insert -- thereof; --, therefor.

Column 18
Line 48, delete "Bicinchonic" and insert -- Bicinchoninic --, therefor.

Column 19
Line 38, delete "phosphoric" and insert -- phosphonitrilic --, therefor.

Column 20
Line 21, delete "(Plasma Therm," and insert -- (PlasmaTherm, --, therefor.

Column 21
Line 53, delete "0.2" and insert -- 0.2. --, therefor.

UNITED STATES PATENT AND TRADEMARK OFFICE
CERTIFICATE OF CORRECTION

PATENT NO.         : 7,658,994 B2                                           Page 1 of 1
APPLICATION NO.    : 10/896392
DATED              : February 9, 2010
INVENTOR(S)        : Brinda B. Lakshmi It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 565 days.

Signed and Sealed this

Thirtieth Day of November, 2010

David J. Kappos
*Director of the United States Patent and Trademark Office*